United States Patent
Dos Santos et al.

(10) Patent No.: US 8,840,578 B2
(45) Date of Patent: Sep. 23, 2014

(54) MULTILAYER MEMBRANE ACTUATORS

(75) Inventors: Cesario P. Dos Santos, Aliso Viejo, CA (US); Michael L. Gelvin, Alta Loma, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 111 days.

(21) Appl. No.: 13/315,905

(22) Filed: Dec. 9, 2011

(65) Prior Publication Data

US 2013/0150775 A1    Jun. 13, 2013

(51) Int. Cl.
*A61F 9/00* (2006.01)
*A61F 9/007* (2006.01)
*A61M 27/00* (2006.01)
*A61M 5/142* (2006.01)
*A61M 5/145* (2006.01)

(52) U.S. Cl.
CPC ..... *A61F 9/00781* (2013.01); *A61F 2210/0076* (2013.01); *A61F 9/0017* (2013.01); *A61F 9/007* (2013.01); *A61M 27/002* (2013.01); *A61M 2202/04* (2013.01); *A61M 2205/8231* (2013.01); *A61M 5/14276* (2013.01); *A61M 2005/14513* (2013.01); *A61M 2210/0612* (2013.01); *A61M 2202/0014* (2013.01); *A61M 2005/14204* (2013.01)
USPC .......... 604/9; 604/8; 604/10; 604/65; 604/66; 604/245; 604/246; 604/247; 604/540; 623/4.1; 623/5.11

(58) Field of Classification Search
CPC ......... A61M 2005/14204; A61M 2005/14513; A61M 5/155; A61M 5/14593; A61M 2210/0612; A61M 27/002; A61M 2027/002; A61M 2202/0014; A61M 2202/04; A61M 5/14276; A61M 2205/8231; A61F 9/00781; A61F 9/007; A61F 9/0017; A61F 2210/0076
USPC ......... 604/890.1, 891.1, 892.1; 623/4.1, 5.11, 623/23.64
See application file for complete search history.

(56) References Cited

U.S. PATENT DOCUMENTS 4,089,329 A    5/1978    Couvillon et al.
4,206,762 A    6/1980    Cosman
(Continued)

FOREIGN PATENT DOCUMENTS

DE    4438201    5/1996
EP    2427097    3/2012
(Continued)

OTHER PUBLICATIONS

Vitali Parkhutik, Eduardo Andrade Ibarra, "The role of hydrogen in the formation of porous structures in silicon." Materials Science and Engineering: B, vol. 58, Issues 1-2, Feb. 12, 1999, pp. 95-99, ISSN 0921-5107. (http://www.sciencedirect.com/science/article/pii/S0921510798002979). accessed Monday, Jul. 22, 2013.*

(Continued)

Primary Examiner — Adam Marcetich
(74) Attorney, Agent, or Firm — Kenneth D. Bassinger

(57) ABSTRACT

An IOP control device for implantation in an eye of a patient is disclosed. The device includes a housing and a multilayer membrane. The housing is sized for implantation into the eye and includes an entrance port and an exit port. The membrane is anchored within the housing to form a flow control chamber on a first side and a fluid flow passageway on a second opposing side of the membrane. The chamber is arranged to contain a gas creating a chamber pressure, and the membrane is configured to affect flow through the passageway from the entrance port to the exit port by deflecting in response to changes in the chamber pressure. The membrane comprises a first layer having a higher permeability and a higher flexibility than the second layer, which is disposed adjacent the first layer and restricts the diffusion of gas in the chamber through the membrane.

9 Claims, 2 Drawing Sheets

(56) References Cited

U.S. PATENT DOCUMENTS

| | | | |
|---|---|---|---|
| 4,457,757 A | 7/1984 | Molteno | |
| 4,656,827 A | 4/1987 | Puillet | |
| 4,750,901 A | 6/1988 | Molteno | |
| 4,869,282 A * | 9/1989 | Sittler et al. | 137/15.01 |
| 4,922,913 A | 5/1990 | Waters et al. | |
| 5,005,577 A | 4/1991 | Frenkel | |
| 5,083,742 A * | 1/1992 | Wylie et al. | 251/61.1 |
| 5,178,604 A | 1/1993 | Baerveldt | |
| 5,179,953 A | 1/1993 | Kursar | |
| 5,397,300 A | 3/1995 | Baerveldt | |
| 5,466,233 A | 11/1995 | Weiner et al. | |
| 5,476,445 A | 12/1995 | Baerveldt | |
| 5,558,629 A | 9/1996 | Baerveldt | |
| 5,702,618 A * | 12/1997 | Saaski et al. | 216/2 |
| 5,707,643 A | 1/1998 | Ogura et al. | |
| 5,891,097 A * | 4/1999 | Saito et al. | 604/141 |
| 5,910,110 A | 6/1999 | Bastable | |
| 6,007,511 A | 12/1999 | Prywes | |
| 6,048,328 A * | 4/2000 | Haller et al. | 604/288.03 |
| 6,251,090 B1 | 6/2001 | Avery et al. | |
| 6,447,449 B1 | 9/2002 | Fleischman et al. | |
| 6,468,283 B1 | 10/2002 | Richter et al. | |
| 6,579,235 B1 | 6/2003 | Abita et al. | |
| 6,589,198 B1 | 7/2003 | Soltanpour et al. | |
| 6,682,500 B2 | 1/2004 | Soltanpour et al. | |
| 6,712,764 B2 | 3/2004 | Jeffries et al. | |
| 6,719,750 B2 | 4/2004 | Varner et al. | |
| 6,749,568 B2 | 6/2004 | Fleischman et al. | |
| 6,939,299 B1 | 9/2005 | Petersen et al. | |
| 6,976,982 B2 | 12/2005 | Santini et al. | |
| 7,137,952 B2 | 11/2006 | Leonardi et al. | |
| 7,169,106 B2 | 1/2007 | Fleischman et al. | |
| 7,252,006 B2 | 8/2007 | Tai et al. | |
| 7,354,416 B2 | 4/2008 | Quiroz-Mercado et al. | |
| 7,409,863 B2 | 8/2008 | Bateman et al. | |
| 7,612,328 B2 | 11/2009 | Kaiser | |
| 7,756,559 B2 | 7/2010 | Abreu | |
| 8,182,435 B2 | 5/2012 | Dacquay et al. | |
| 8,257,295 B2 | 9/2012 | Rickard et al. | |
| 8,419,673 B2 | 4/2013 | Rickard | |
| 2001/0000527 A1 | 4/2001 | Yaron et al. | |
| 2002/0019607 A1 | 2/2002 | Bui | |
| 2002/0049374 A1 | 4/2002 | Abrea | |
| 2002/0099359 A1 | 7/2002 | Santini, Jr. et al. | |
| 2002/0103412 A1* | 8/2002 | Trimmer | 600/16 |
| 2002/0139947 A1* | 10/2002 | Wang | 251/61 |
| 2002/0143284 A1 | 10/2002 | Tu et al. | |
| 2002/0156461 A1* | 10/2002 | Joshi | 604/891.1 |
| 2002/0175191 A1* | 11/2002 | Joshi et al. | 222/386 |
| 2002/0193674 A1 | 12/2002 | Fleischman et al. | |
| 2003/0014036 A1 | 1/2003 | Varner et al. | |
| 2003/0078487 A1 | 4/2003 | Jeffries | |
| 2003/0225318 A1 | 12/2003 | Montegrande et al. | |
| 2004/0059248 A1 | 3/2004 | Messner et al. | |
| 2004/0073137 A1 | 4/2004 | Lloyd et al. | |
| 2004/0111050 A1 | 6/2004 | Smedley et al. | |
| 2004/0116794 A1 | 6/2004 | Fink et al. | |
| 2004/0186367 A1 | 9/2004 | Fresco | |
| 2004/0254438 A1 | 12/2004 | Chuck et al. | |
| 2004/0254517 A1 | 12/2004 | Quiroz-Mercado | |
| 2005/0016866 A1* | 1/2005 | Kramer et al. | 205/637 |
| 2005/0049578 A1 | 3/2005 | Tu et al. | |
| 2005/0159660 A1 | 7/2005 | Montegrande et al. | |
| 2005/0271704 A1 | 12/2005 | Tu et al. | |
| 2005/0273033 A1 | 12/2005 | Grahn et al. | |
| 2006/0131350 A1 | 6/2006 | Schechter et al. | |
| 2007/0019156 A1 | 1/2007 | Fink | |
| 2007/0032757 A1 | 2/2007 | Medow | |
| 2007/0077270 A1 | 4/2007 | Wen | |
| 2007/0106199 A1 | 5/2007 | Krivoy et al. | |
| 2007/0109117 A1 | 5/2007 | Heitzmann et al. | |
| 2007/0123767 A1 | 5/2007 | Montegrande et al. | |
| 2007/0129623 A1 | 6/2007 | Fleischman et al. | |
| 2007/0212397 A1 | 9/2007 | Roth | |
| 2007/0255262 A1* | 11/2007 | Haase | 604/891.1 |
| 2008/0015421 A1 | 1/2008 | Penner | |
| 2008/0027478 A1 | 1/2008 | Connors et al. | |
| 2008/0077127 A1 | 3/2008 | Gao et al. | |
| 2008/0097276 A1 | 4/2008 | Bertrand et al. | |
| 2008/0125691 A1 | 5/2008 | Yaron et al. | |
| 2008/0129486 A1 | 6/2008 | Jeckelmann et al. | |
| 2008/0147021 A1 | 6/2008 | Jani | |
| 2008/0228127 A1 | 9/2008 | Burns et al. | |
| 2008/0257915 A1* | 10/2008 | Wold | 222/389 |
| 2009/0069648 A1 | 3/2009 | Irazqui et al. | |
| 2009/0076367 A1 | 3/2009 | Sit et al. | |
| 2009/0143713 A1 | 6/2009 | Dam et al. | |
| 2009/0227933 A1 | 9/2009 | Karageozian | |
| 2009/0240215 A1 | 9/2009 | Humayun et al. | |
| 2009/0275924 A1 | 11/2009 | Latanzio et al. | |
| 2009/0312742 A1 | 12/2009 | Pang et al. | |
| 2010/0010416 A1 | 1/2010 | Juan, Jr. et al. | |
| 2010/0042209 A1 | 2/2010 | Guarnieri | |
| 2010/0121348 A1 | 5/2010 | Van Der Burg et al. | |
| 2010/0174272 A1 | 7/2010 | Weiner | |
| 2010/0222769 A1 | 9/2010 | Meng et al. | |
| 2010/0222770 A1* | 9/2010 | Gordon et al. | 604/891.1 |
| 2010/0234717 A1 | 9/2010 | Wismer | |
| 2010/0253167 A1 | 10/2010 | Charnley et al. | |
| 2010/0305550 A1* | 12/2010 | Meng et al. | 604/891.1 |
| 2011/0046536 A1 | 2/2011 | Stegmann et al. | |
| 2011/0071454 A1 | 3/2011 | Dos Santos et al. | |
| 2011/0071505 A1* | 3/2011 | Rickard et al. | 604/540 |
| 2011/0248671 A1 | 10/2011 | Dos Santos | |

FOREIGN PATENT DOCUMENTS

| | | |
|---|---|---|
| WO | WO 93/03665 | 3/1993 |
| WO | 9803809 | 1/1998 |
| WO | WO 98/03665 | 1/1998 |
| WO | 9938470 | 8/1999 |
| WO | 0194784 | 12/2001 |
| WO | WO 03/001991 | 1/2003 |
| WO | WO 03/102632 | 12/2003 |
| WO | 2005088417 | 9/2005 |
| WO | 2007127305 | 11/2007 |
| WO | WO 2007/136993 | 11/2007 |
| WO | 2008061043 | 5/2008 |
| WO | 2008084350 | 7/2008 |
| WO | 2009010799 | 1/2009 |
| WO | WO 2009/026499 | 2/2009 |
| WO | WO 2009/049686 | 4/2009 |
| WO | WO 2009/081031 | 7/2009 |
| WO | 2010129446 | 11/2010 |
| WO | 2011034727 | 3/2011 |
| WO | 2011034738 | 3/2011 |
| WO | 2011034740 | 3/2011 |
| WO | 2011034742 | 3/2011 |
| WO | 2011035218 | 3/2011 |
| WO | 2012012017 | 1/2012 |

OTHER PUBLICATIONS

"Walter, Peter; Intraocular Pressure Sensor: Where Are We—Where Will We Go? Journal Graefe's Archive for Clinical and Experimental Ophthalmology; Publisher Springer Berline/Heidelberg; ISSN 0721-832X (Print) 1435-702X (Online); Issue vol. 240, No. 5/May, 2002 DOI 10.1007/s00417-002-0474-y; pp. 335-336; Subject Collection Medicine."

Eggers, T., et al, "Wireless Intra-Ocular Pressure Monitoring System Integrated Into an Artificial Lens," 1st Annual Int'l IEEE-EMBS Special Topic Conference on Microtechnologies in Medicine & Biology, Oct. 12-14, 2000, pp. 466-469, Lyon, France.

Greene, M.E. and Gilman, B.G., "Intraocular Pressure Measurement With Instrumented Contact Lenses," Investigative Ophthalmology & Visual Science (IVOS), Apr. 1974, pp. 299-302, vol. 13, No. 4, IVOS.

Hjortdal, Jesper and Jensen, Peter, "In Vitro Measurement of Corneal Strain, Thickness, and Curvature Using Digital Image Processing," Acta Ophthalmologica Scandinavica, 1995, pp. 5-11, vol. 73, Denmark.

Lam, Andrew K.C. and Douthwaite, William A., "The Effect of an Artificially Intraocular Pressure on the Central Corneal Curvature,"

(56) References Cited

OTHER PUBLICATIONS

Ophthalmic and Physiological Optics, 1997, pp. 18-24, vol. 17, No. 1, Elsevier Science, Ltd., Great Britain.
Leonardi, Matteo, et al., "A Soft Contact Lens With a Mems Strain Gage Embedded for Intraocular Pressure Monitoring," In Proc. 12th Int'l Conference on Solid State Sensors, Actuators and Microsystems, Jun. 8-12, 2003, pp. 1043-1046, vol. 2, Boston, MA.
Leonardi, Matteo, et al., "First Steps Toward Noninvasive Intraocular Pressure Monitoring with a Sensing Contact Lens," Investigative Ophthalmology & Visual Science (IVOS), 2004, pp. 3113-3117, vol. 45, No. 9, IVOS.
McLaren, Jay W., et al, "Continuous Measurement of Intraocular Pressure in Rabbits by Telemetry," Investigative Ophthalmology & Visual Science (IVOS), May 1996, pp. 966-975, vol. 37, No. 6, IVOS.
Mokwa, Wilfried, et al, "Micro-Transponder Systems for Medical Applications," IEEE Transactions on Instrumentation and Measurement, Dec. 2001, pp. 1551-1555, vol. 50, No. 6, IEEE, Germany.
Puers, Robert, "Linking Sensors with Telemetry: Impact on the System Design," In Proc. 8th Int'l Conference of Solid State Sensors, Actuators, Eurosens, Jun. 25-29, 1995, pp. 169-174, Stockholm, Sweden.
Schnakenberg, U., et al, "Initial Investigations on Systems for Measuring Intraocular Pressure," Sensors and Actuators, 2000, p. 287-291, vol. 85, Elsevier Science B.V., Germany.
Stangel, Karsten, et al, "A Programmable Intraocular CMOS Pressure Sensor System Implant," IEEE Journal of Solid-State Circuits, Jul. 2001, pp. 1094-1100, vol. 36, No. 7, IEEE, Germany.
Van Schuylenbergh, K., et al, "An Implantable Telemetric Tonometer for Direct Intraocular Pressure Measurements," 1st European Conference on Biomedical Engineering, Feb. 1991, pp. 194-195, vol. 17, No. 20, Nice, France.
Byunghoon Bae, Hongseok Kee, Seonho Kim, Yeon Lee, Taeseok Sim, Yongkweon Him and Kyihwan Park; "In Vitro Experiment of the Pressure Regulating Valve for a Glaucoma Impact"; Journal of Micromechanics and Microengineering, 13 (2003); pp. 613-619.
International Searching Authority, Search Report and Written Opinion of the International Searching Authority, PCT/US2010/033329, Jul. 13, 2010, 14 pages.
International Searching Authority, Search Report and Written Opinion of the International Searching Authority, PCT/US2010/047600, Dec. 14, 2010, 13 pages.
International Searching Authority, Search Report and Written Opinion of the International Searching Authority, PCT/US2010/047429, Nov. 1, 2010, 15 pages.
International Searching Authority, Search Report and Written Opinion of the International Searching Authority, PCT/US2010/049424, Nov. 26, 2010, 15 pages.
International Searching Authority, Search Report of the International Searching Authority, PCT/US2011/036742, Aug. 17, 2011, 2 pages.
Ullerich, Stella, et al, "Micro Coils for an Advanced System for Measuring Intraocular Pressure," 1st Annual Int'l IEEE-EMBS Special Topic Conference on Microtechnologies in Medicine & Biology, Oct. 12-14, 2000, pp. 470-474, Lyon, France.
Neagu Cristina R.; "A Medical Microactuator Based on an Electrochemical Principle"; Thesis at the Twente University,the Netherlands, Enschede; Aug. 28, 1998; pp. 1-162.
Saloomeh Saati MD., Ronalee Lo PhD, Po-Ying Li PhD, Ellis Meng PhD, Rohit Varma MD MPH, and Mark S. Humayun MD PhD; "Mini Drug Pump for Ophthalmic Use"; TRANS Am Ophthalmol Soc 2009; 107; pp. 60-71.
Erik Stemme and Goran Stemme; "A Valveless Diffuser/Nozzle-Based Fluid Pump"; ScienceDirect; Sensors and Actuators A, 39 (1993); pp. 159-167.
Nisar A., Afzulpurkar Nitin, Mahaisavariya Banchong, and Tuantranont Adisorn; "MEMS-Based Micropumps in Drug Delivery and Biomedical Applications"; ScienceDirect; Sensors and Acuators B 130 (2008) pp. 917-942.
International Search Report and Written Opinion corresponding to PCT/US2012/067741 dated Apr. 2, 2013.
International Search Report and Written Opinion corresponding to PCT/US2010/047605 dated Dec. 16, 2010.
International Search Report and Written Opinion corresponding to PCT/US2010/047612 dated Dec. 21, 2010.
Driot et al.; "Ocular pharmacokinetics of fluocinolone acetonide after RetisertTM intravitreal implantation in rabbits over a 1-year period"; J. Ocular Pharm; vol. 20; No. 3; pp. 269-275 (2004).
Glybina et al.; "Neuroprotective properties of fluocinolone acetonide chronically delivered into the vitreous of albino RCS rats"; IVOS; vol. 47; ARVO E-Abstract 1028 (2006).
Kupperman et al.; "Efficacy and safety of a novel intravitreous dexamethasone drug-delivery system after applicator or incisional placement in patients with macular edema"; IVOS; vol. 47; ARVO E-Abstract 5913 (2006).
Miyamoto et al.; "Biodegradable scleral implant for intravitreal controlled release of fluconazole"; Current Eye Res.; vol. 16; No. 19; pp. 930-935 (1997).
Miruthyunjaya et al.; "An intravitreal sustained release fluocinolone acetonide device to treat severe experimental uveitis"; IVOS; vol. 44; ARVO E-Abstract 4215 (2003).
Ratanapakorin et al.; "Helical intravitreal triamcinolone implant: an explanation survival study"; IVOS; vol. 46; ARVO E-Abstract 484 (2005).
Rego et al; "In vitro evaluation of sustained-release intravitreal dexamethasone implants"; IVOS; vol. 45; ARVO E-Abstract 5060 (2004).
Sakurai et al.; "Scleral plug of biodegradable polymers containing ganciclovir for experimental cytomegalovirus retinitis"; IVOS; vol. 42; No. 9; pp. 2043-2048 (2004).
See et al.; "Safety and drug release profile of injectable intravitreal sustained-release fluocinolone acetonide device"; IVOS; vol. 47; ARVO E-Abstract 5119 (2006).
Tano et al.; "Helical intravitreal implant: surgical method development and outcomes"; IVOS; vol. 46; ARVO E-Abstract 483 (2005).
Varner et al.; "Development of a minimally invasive intravitreal implant for drug delivery"; IVOS; vol. 44; ARVO E-Abstract 4214 (2003).
Weiner; "Drug delivery systems in ophthalmic applications; In Ocular Therapeutics; Eye on New Discoveries; T. Yorio, A. Clark, M. Wax, Eds, Elsevier Press/Academic Press, New York", pp. 7-43 (2007).
Yasukawa et al.; "Biodegradable scleral plugs for vitreoretinal drug delivery"; Adv. Drug Del. Rev.; vol. 52; No. 1; pp. 25-36 (2001).
International Search Report and Written Opinion corresponding to PCT/US2012/068878 dated Apr. 3, 2013.
International Search Report and Written Opinion corresponding to PCT/US2012/067747 dated Apr. 2, 2013.

\* cited by examiner

MULTILAYER MEMBRANE ACTUATORS

BACKGROUND

The present disclosure relates generally to valves and associated systems and methods for use in ophthalmic treatments. In some instances, embodiments of the present disclosure are configured to be part of an IOP control system.

Glaucoma, a group of eye diseases affecting the retina and optic nerve, is one of the leading causes of blindness worldwide. Most forms of glaucoma result when the intraocular pressure (IOP) increases to pressures above normal for prolonged periods of time. IOP can increase due to high resistance to the drainage of the aqueous humor relative to its production. Left untreated, an elevated IOP causes irreversible damage to the optic nerve and retinal fibers resulting in a progressive, permanent loss of vision.

FIG. 1 is a diagram of the front portion of an eye that helps to explain the processes of glaucoma. In FIG. 1, representations of the lens 110, cornea 120, iris 130, ciliary body 140, trabecular meshwork 150, and Schlemm's canal 160 are pictured. Anatomically, the anterior segment of the eye includes the structures that cause elevated IOP which may lead to glaucoma. Aqueous humor fluid is produced by the ciliary body 140 that lies beneath the iris 130 and adjacent to the lens 110 in the anterior segment of the eye. This aqueous humor washes over the lens 110 and iris 130 and flows to the drainage system located in the angle of the anterior chamber. The angle of the anterior chamber, which extends circumferentially around the eye, contains structures that allow the aqueous humor to drain. The trabecular meshwork 150 is commonly implicated in glaucoma. The trabecular meshwork 150 extends circumferentially around the anterior chamber. The trabecular meshwork 150 seems to act as a filter, limiting the outflow of aqueous humor and providing a back pressure that directly relates to IOP. Schlemm's canal 160 is located beyond the trabecular meshwork 150. Schlemm's canal 160 is fluidically coupled to collector channels (not shown) allowing aqueous humor to flow out of the anterior chamber. The two arrows in the anterior segment of FIG. 1 show the flow of aqueous humor from the ciliary bodies 140, over the lens 110, over the iris 130, through the trabecular meshwork 150, and into Schlemm's canal 160 and its collector channels.

One method of treating glaucoma includes implanting a drainage device in a patient's eye. The drainage device allows fluid to flow from the interior chamber of the eye to a drainage site, relieving pressure in the eye and thus lowering IOP. In order to provide consistency and accuracy in fluid flow through the drainage device, it may be important to limit changes and degradation that may occur in the drainage device over time.

The system and methods disclosed herein overcome one or more of the deficiencies of the prior art.

SUMMARY

In one exemplary aspect, this disclosure is directed to an IOP control system or implant that protects against under-drainage while simultaneously guarding against over-drainage, and consequently minimizes bleb formation and subsequent fibrotic changes. For example, IOP control systems or implants that utilize electrolysis-based membrane valves can provide flow control through the drainage device. Such membrane valves utilize deflection of the membrane in response to pressure differentials across the membrane to regulate the flow through the drainage device. These pressure differentials may be obtained using phase-change processes that convert liquid to gas. However, gas molecules in membrane valves may diffuse through the membrane. As gas is lost through the membrane, a gas imbalance arises due to the unequal diffusion rates of various gases (e.g., hydrogen and oxygen). Such valves require a constant supply of power to continuously generate enough gas by electrolysis to overcome the loss of gas through the membrane in order to maintain a desired state (e.g., a state in which a particular gas level is required to sustain desired membrane deflection).

Accordingly, the present disclosure describes a membrane that may slow or prevent the escape of gas through the membrane. In particular, this disclosure describes a membrane actuator capable of slowing or preventing the escape of gas in an electrolysis-based ocular device.

In one exemplary aspect, the present disclosure is directed to an IOP control device for implantation in an eye of a patient. The IOP control device includes a housing and a multilayer membrane. The housing is sized for implantation into the eye of the patient and includes an entrance port and an exit port. The multilayer membrane is anchored within the housing in a manner forming a flow control chamber on a first side of the multilayer membrane and a fluid flow passageway on a second opposing side of the membrane. The flow control chamber is arranged to contain a gas creating a flow control chamber pressure, and the multilayer membrane is configured to affect flow through the fluid flow passageway from the entrance port to the exit port by deflecting in response to changes in the flow control chamber pressure. The multilayer membrane comprises a first layer having a higher permeability and a higher flexibility, and a second layer having a lower permeability and a lower flexibility. The second layer is disposed adjacent the first layer and restricts the diffusion of gas in the chamber through the multilayer membrane.

In another exemplary aspect, the present disclosure is directed to an IOP control system for implantation in an eye of a patient. The IOP control system includes a drainage tube configured to convey aqueous humor from an anterior chamber of the eye and an electrolysis-based implantable device in fluid communication with the drainage tube. The electrolysis-based implantable device includes a multilayer membrane that is anchored within the implantable device to form a flow control chamber on a first side of the multilayer membrane. The implantable device is actuatable in response to a flow control chamber pressure, and the membrane is configured to control flow rates of the aqueous humor along the drainage tube by deflecting in response to the flow control chamber pressure.

In another exemplary embodiment, the present disclosure is directed to a method of regulating drainage from an anterior chamber of an eye with an implantable device. The methods includes directing fluid through a fluid flow passageway formed in part by a flexible, multilayer membrane that comprises at least one base layer and at least one regulating layer shaped and configured to reduce gas permeability through the membrane. The method further includes modifying the amount of drainage through the implantable device in response to a flow control pressure acting on the multilayer membrane by deflecting the membrane to increase or decrease the size of the fluid flow passageway in the membrane valve.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and methods disclosed herein and together with the description, serve to explain the principles of the present disclosure.

DETAILED DESCRIPTION

Figure 1:
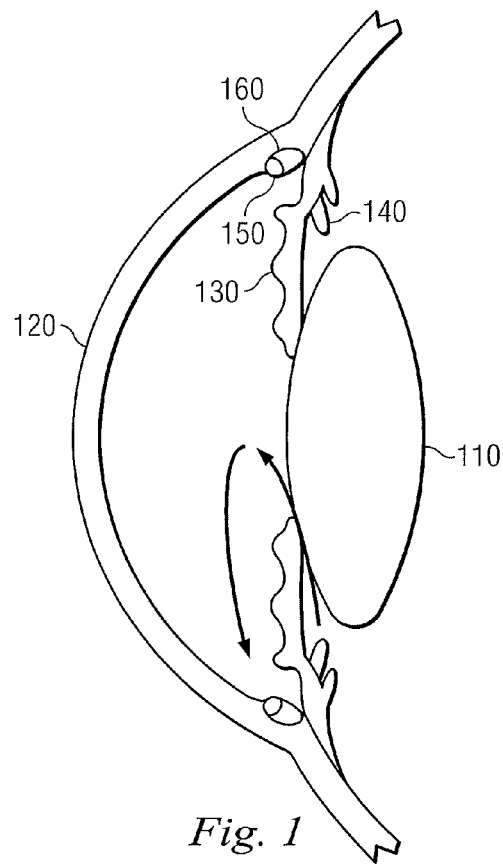
FIG. 1 is a diagram of the front portion of an eye.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For simplicity, in some instances the same reference numbers are used throughout the drawings to refer to the same or like parts.

The present disclosure relates generally to multilayer membrane actuators used in the operation of electrolysis-based membrane valves. In some instances, embodiments of the present disclosure are configured to be part of an IOP control system. Those of skill in the art will realize that the multilayer membrane actuators disclosed herein may be utilized in similar applications requiring minimal or selective gas diffusion through a membrane.

The membrane actuators disclosed herein are formed of multiple layers and are configured to regulate the passage of gas across the membrane by preventing or slowing the inadvertent escape of gas through the membrane. Thus, by preventing inadvertent gas losses across the membrane (and subsequent gas recombination), the multilayer membrane actuators disclosed herein work to reduce or avoid the gas imbalance that may arise in IOP control systems utilizing electrolysis-based valves with single-layer membrane actuators. The incorporation of an impermeable or selectively permeable layer in the membrane actuator allows for selective gas permeability, thereby increasing the longevity and reliability of valve actuation by allowing the gas molecular ratio within the electrolysis chamber to stay in balance. Thus, the multilayer membrane actuators disclosed herein may improve or optimize the performance of electrolysis-based valves utilizing membrane actuators within an IOP control system.

Figure 2:
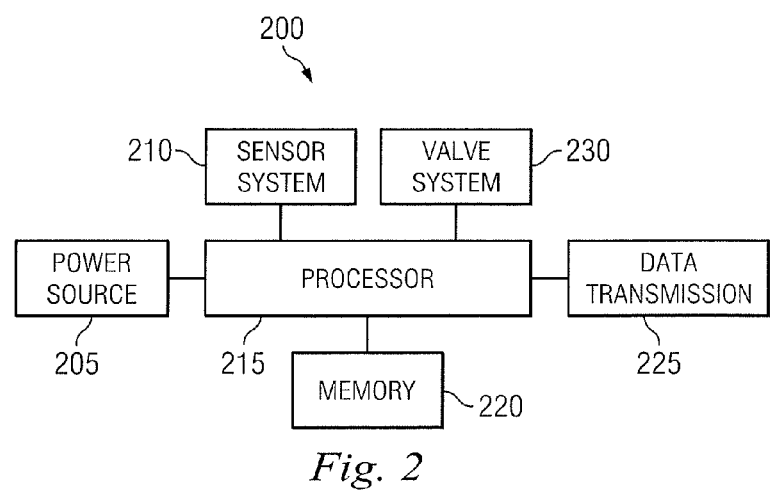
FIG. 2 is a block diagram of an exemplary IOP control system according to the principles of the present disclosure.

FIG. 2 is a block diagram of an exemplary IOP control system 200 implantable in an eye of a patient for the treatment of glaucoma or other conditions. The IOP control system 200 is configured in a manner that provides IOP pressure control, but also regulates and controls bleb pressures, reducing complications arising from surgical implant glaucoma treatments. In FIG. 2, the IOP control system 200 includes a power source 205, an IOP sensor system 210, a processor 215, a memory 220, a data transmission module 225, and a valve system 230.

The power source 205, which provides power to the system 200, is typically a rechargeable battery, such as a lithium ion or lithium polymer battery, although other types of batteries may be employed. The power source can be recharged via inductive coupling such as an RFID link or other type of magnetic coupling.

The processor 215 is typically an integrated circuit with power, input, and output pins capable of performing logic functions. In various embodiments, the processor 215 may be a targeted device controller or a microprocessor configured to control more than one component of the device.

The memory 220, which is typically a semiconductor memory such as RAM, FRAM, or flash memory, interfaces with the processor 215. As such, the processor 215 can write to and read from the memory 220, and perform other common functions associated with managing semiconductor memory. In this manner, a series of IOP readings can be stored in the memory 220.

The data transmission module 225 may employ any of a number of different types of data transmission. For example, in various embodiments, the data transmission module 225 may be an active device such as a radio or a passive device with an antenna on an RFID tag. Alternatively, the data transmission module 225 may be activated to communicate an elevated IOP condition to a secondary device such as a PDA, cell phone, computer, wrist watch, custom device exclusively for this purpose, remote accessible data storage site (e.g. an internet server, email server, text message server), or other electronic device or service.

The IOP sensor system 210 is described below with reference to FIG. 3, and the valve system 230 is described below with reference to FIGS. 4 and 5.

Figure 3:
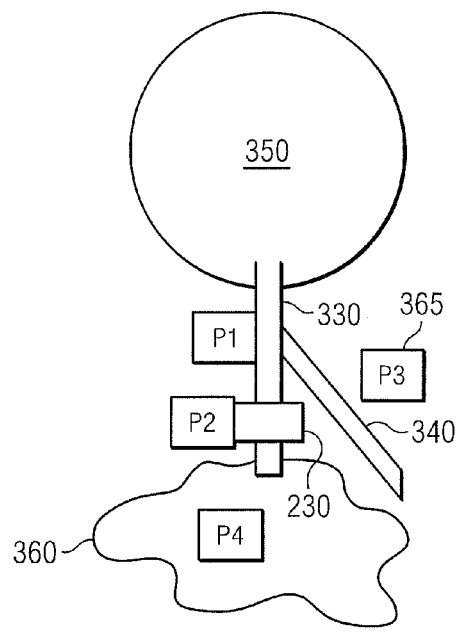
FIG. 3 is a schematic diagram of an exemplary IOP control system according to the principles of the present disclosure.

FIG. 3 is a diagram of the exemplary IOP sensor system 210, a drainage tube 330, the valve system 230, and a divider 340. In FIG. 3, the exemplary IOP sensor system 210 includes four pressure sensors, P1, P2, P3, and P4. The pressure sensor P1 is located in or is in fluidic communication with an anterior chamber identified by the reference number 350, the pressure sensor P2 is located to measure intermediate pressures found within the valve system 230, the pressure sensor P3 is located remotely from P1 and P2 in manner to measure atmospheric pressure, and the pressure sensor P4 is located at a drainage site 360 in the subconjunctival space and is arranged to measure bleb pressure.

In some embodiments, the pressure sensor P1 is located in a lumen or tube that is in fluid communication with the anterior chamber. The pressure sensor P4 may be located in a pocket, such as a bleb, that generally contains aqueous humor or in communication with such a pocket, via a tube for example, and is in the wet site 360. The drainage site 360 may be, by way of non-limiting example, in a subconjunctival space, a suprachoroidal space, a subscleral space, a supraciliary space, Schlemm's canal, a collector channel, an episcleral vein, and a uveo-scleral pathway, among other locations in the eye.

The drainage tube 330 drains aqueous humor from the anterior chamber 350 of the eye. The valve system 230 controls the flow of aqueous humor through the tube 330. In the embodiment shown, the pressure sensor P1 measures the pressure in the tube 330 upstream from the valve system 230 and downstream from the anterior chamber 350. In this manner, pressure sensor P1 measures the pressure in the anterior chamber 350. The expected measurement discrepancy between the true anterior chamber pressure and that measured by P1 when located in a tube downstream of the anterior chamber (even when located between the sclera and the conjunctiva) is very minimal. For example, Poiseuille's law for pipe flow predicts a pressure drop of 0.01 mmHg across a 5-millimeter long tube with a 0.300 millimeter inner diameter for a flow rate of 3 microliters per minute of water.

In some embodiments, the system includes barriers that separate the sensors P1, P2, P3, and P4. These barriers may be elements of the system itself. For example, in FIG. 3, the pressure sensor P3 is physically separated from the pressure sensor P4 by the divider 340. The divider 340 is a physical structure that separates the wet site 360 of P4 from the dry site 365 of P3. In one example, the barrier separating the anterior chamber pressure sensor P1 and the drainage site pressure sensor P4 is the valve system 230.

Generally, IOP is a gauge pressure reading—the difference between the absolute pressure in the eye (as measured by P1) and atmospheric pressure (as measured by P3). In one embodiment of the present disclosure, pressure readings are taken by the pressure sensors P1 and P3 simultaneously or nearly simultaneously over time so that the actual IOP can be calculated (as P1−P3 or P1−f(P3), where f(P3) indicates a function of P3). The pressure readings of P1 and P3 can be stored in memory 220 by the processor 215. They can later be read from memory so that actual IOP over time can be interpreted by a physician.

The pressure sensors P1, P2, P3, and P4 can be any type of pressure sensors suitable for implantation in the eye. They each may be the same type of pressure sensor, or they may be different types of pressure sensors.

Since the pressure sensor P1 measures the pressure in the anterior chamber 350 and pressure sensor P4 measures pressure at the drainage site 360, the difference between the readings taken by these two pressure sensors (P1-P4) provides an indication of the pressure differential between the anterior chamber 350 and the drainage site 360. In one embodiment, this pressure differential dictates the rate of aqueous humor flow from the anterior chamber 350 to the drainage site 360.

Readings from the pressure sensors P1, P2, P3, and P4 can be used to control the flow rate through the tube 330 by controlling the valve system 230. For example, the valve system 230 may be controlled based on the pressure readings from pressure sensors P1, P2, P3, and P4. The valve system 230 may be controlled by microprocessor 215 based on input data received from the sensors. A desired pressure differential (that corresponds to a desired flow rate) can be maintained by controlling the operation of the valve system 230. Likewise, various intraocular pressure parameters, such as, by way of non-limiting example, the desired IOP, the IOP change rate, and/or the bleb pressure may be controlled by controlling the operation of valve system 230. Note that the physician would be able to set the high/low IOP thresholds wirelessly to meet each patient's specific requirements.

Figure 4:
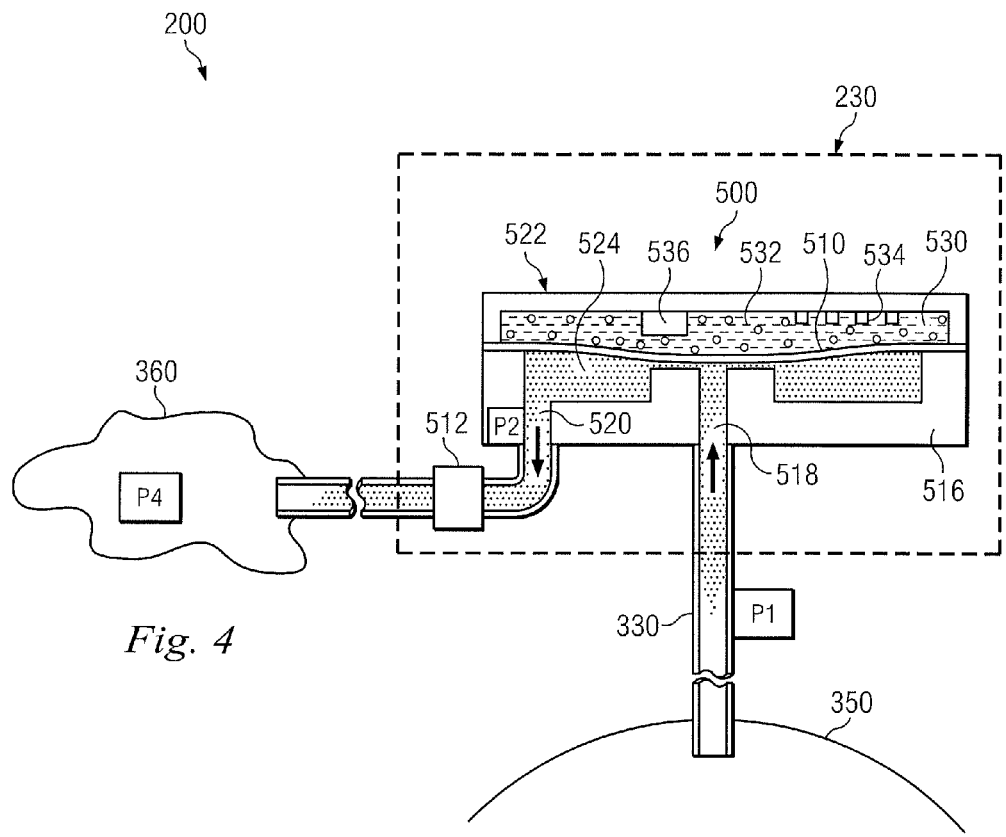
FIG. 4 is an illustration of a cross-sectional view of an exemplary IOP control system according to one embodiment consistent with the principles of the present disclosure.

FIG. 4 shows an exemplary embodiment of a membrane valve 500 that may form a part of the valve system 230. The valve system 230 is disposed along, and may form a part of, the drainage tube 330 between the tube end in the anterior chamber 350 and the drainage site 360, as shown in FIG. 3.

The valve system 230 is configured to control the flow of drainage fluid through the drainage tube 330, and thereby control pressure in the eye, including the IOP. For example, when IOP is high, the valve system 230 may operate to permit increased flow through the drainage tube, and when IOP is low, the valve system 230 may operate to decrease the flow through the drainage tube. In addition, the valve system 230 is configured to monitor and control the flow of drainage fluid to the bleb, and thereby control the bleb pressure to maintain a desired fluid flow to the bleb. This may decrease fibrosis and increase absorption efficiency. To accomplish this, the valve system 230 is responsive to signals sent as instructions from the processor 215, shown in FIG. 2. The processor 215 is responsive to pressure measurements taken by the pressure sensors P1, P2, P3, and P4, and/or the IOP as determined by detected pressures, as explained above.

In the example shown in FIG. 4, the membrane valve 500 includes a multilayer membrane actuator 510. Fluid flows from the drainage tube 330 into and through the membrane valve 500 and any other structures 512, such as, by way of non-limiting example, valves, pumps, and/or check valves, and then exits the valve system 230 to enter the drainage site 360. The structures 512 may include a multilayer membrane actuator similar to the membrane 510. Various embodiments of the valve system 230 may include any number of structures 512. Some embodiments lack any structures 512.

As shown in FIG. 4, the membrane valve 500 includes a housing 516 with an entrance port 518 and an exit port 520, a flow control system 522 in the housing 516, and a fluid flow passageway 524 extending between the entrance port 518 and the exit port 520. The entrance port 518 connects to the drainage tube 330 and is configured to receive aqueous humor flowing from the drainage tube 330 into the valve system 230. The exit port 520 permits fluid to exit the housing 516 for further regulation within the other structures 512 or for release at the drainage site 360.

In addition, the membrane valve 500 includes a flow control chamber 530, actuator fluid 532 in the flow control chamber 530, electrodes 534 arranged to cooperate with the actuator fluid 532, a diffusion barrier 536 in the flow control chamber 530, and the multilayer membrane actuator 510 anchored to the housing 516. In the example shown, the flow control chamber 530 is formed in the housing 516 with rigid structure on three sides. The chamber 530 is sealed closed and separated from the fluid flow passageway 524 by the multilayer membrane actuator 510. Accordingly, as pressure increases within the chamber 530, the membrane 510 displaces in the direction of the fluid flow passageway 524.

In other embodiments, the flow control chamber 530 may be formed of less rigid materials, and expansion may occur in more than one direction. In accordance with this, in some examples the fluid flow passageway 524 includes flexible membrane material that may displace to affect fluid flow through the passageway 524 from more than one direction. For example, in some examples, the multilayer membrane 510 is disposed on two sides of the passageway. In some of these examples the sides are on opposing sides of the passageway. Some of these embodiments may have two or more separate membranes that cooperate to limit the cross-sectional area of the fluid flow passageway 524.

The actuator fluid 532 is contained in the flow control chamber 530 and includes, in some embodiments, water. Some embodiments include a saline such as sodium chloride in solution or other salts.

The electrodes 534 are disposed within the actuator fluid 532 in a manner permitting at least a portion of the ions and electrolytes in the actuator fluid 532 to phase change from liquid to gas, forming gas-filled bubbles through electrolysis. As the bubbles form, the pressure in the chamber 530 increases, thereby increasing the overall pressure. This increased pressure acts on the multilayer membrane 510 to cause its displacement. The electrodes 534 are in electrical communication with the power source 205, which is controlled by the processor 215. Through the electrolysis, water in the actuator fluid 532 may result in hydrogen and oxygen molecules. In the exemplary embodiment shown, the electrodes 534 are interdigitated for efficient and effective electrolysis.

The diffusion barrier 536 within the chamber 530 includes a plurality of small passageways that permit the passage of fluid, but trap or capture gas molecules. This capture process slows the recombination of these molecules, once the molecules are phase-changed from liquid to gas. Accordingly, at least a portion of the actuator fluid 532 may be held in a gaseous state for a sufficient length of time to provide regulatory control of the drainage fluid through the passageway in the valve without a continuous application of energy to the system, thereby reducing the amount of energy required. Some embodiments lack a diffusion barrier.

The multilayer membrane actuator 510 comprises a flexible, deflectable, multilayer membrane. In the example shown, the multilayer membrane 510 is secured to the housing 516 at its edges. Although shown in cross section, the flow control chamber 530 may be disposed to form a circular or cylindrical chamber, with the multilayer membrane 510 being secured along the diameter. Accordingly, the multilayer membrane 510 may be shaped and configured as a generally circular structure that is secured at its periphery to the housing 516. As such, as the volume or pressure increases within the chamber 530, a central portion of the multilayer membrane 510 provides the highest level of displacement or deflection. In other embodiments, the housing and membrane may be formed so that the membrane has a non-circular shape, including oval, substantially rectangular, or square, for example. Other shapes are also contemplated.

Figure 5:
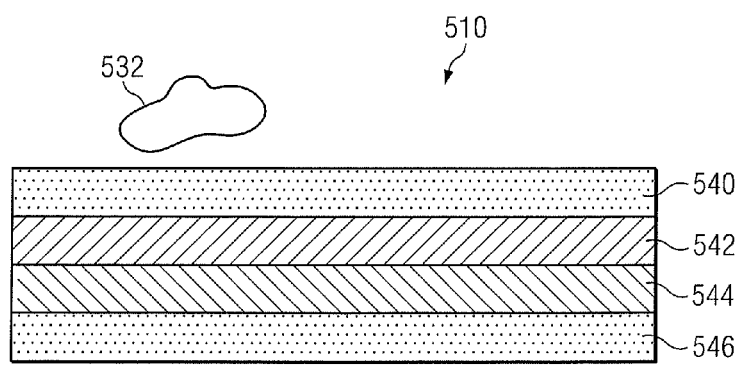
FIG. 5 is an illustration of a cross-sectional view of an exemplary membrane in accordance with one embodiment of the present disclosure.

As shown in FIG. 5, the multilayer, laminate membrane 510 is composed of a composite of layered materials, at least one of which is shaped and configured to regulate the passage of gas through the membrane. In the pictured embodiment, the multilayer membrane 510 includes four composite layers: a first base layer 540, an adherent layer 542, a regulating layer 544, and a second base layer 546, wherein the adherent layer 542 and the regulating layer 544 are sandwiched between the first base layer 540 and the second base layer 546. In the pictured embodiment, the multilayer membrane 510 is positioned within the housing 516 (shown in FIG. 4) such that the first base layer 540 is adjacent the interior of the flow control chamber 530 (i.e., in contact with the actuator fluid 532), and the second base layer 546 is adjacent the fluid flow passageway 524 (i.e., in contact with the intraocular fluid passing through the valve 500). In other embodiments, the multilayer membrane 510 may include any number and arrangement of composite layers. For example, some embodiments may lack any of the first external, adhesive, and second base layers, and other embodiments may include additional layers.

The first base layer 540 and the second base layer 546 may be formed of a biocompatible elastomeric material such as, by way of non-limiting example, Parylene, silicone, silicone nitride, silicone elastomeric, and polyimide.

The regulating layer 544, which is positioned against the elastomeric second base layer 546, comprises the layer regulating gas permeability and may be formed of a material that is less gas permeable (to a particular gas or gases) than the elastomeric materials forming the first external and second base layers 540, 546, respectively. The regulating layer 544 may be impermeable or semipermeable to a particular gas or particular gases. The material for this impermeable or semipermeable layer may be chosen based on the desired gas or gases that should not escape from the flow control chamber 530. For example, suitable materials for the regulating layer 544 that reduce the escape of hydrogen gas include materials such as, by way of non-limiting example, gold, silver, aluminum, and platinum. In some embodiments, the regulating layer 544 is deposited onto the second base layer 546 by vapor deposition.

The optional adherent layer 542 may be formed of a material that provides or enhances adherence between the regulating layer 544 and the first base layer 540. Suitable materials for the adherent layer 542 include materials having adherent properties such as, by way of non-limiting example, titanium and chromium. In some embodiments, the adherent layer 542 is deposited into the membrane actuator 510 by vapor deposition.

The gas permeability of the multilayer membrane is determined by a host of parameters, including without limitation the material composition of the composite layers, especially the regulating layer 544. Certain materials possess greater or less permeability to certain gases over other gases, for example on the basis of molecular size. The particular material chosen for the regulating layer 544 depends upon the particular application of the membrane valve 500. For example, in some electrolysis-based valves utilizing a single chamber with a homogenous, single-layer membrane, hydrogen and oxygen gases are formed in the flow control chamber. Because of the different diffusion rates of hydrogen gas and oxygen gas (due to their vastly different sizes), a gas imbalance can result. In order to account for this gas imbalance, these valves often require a continuous supply of energy to generate sufficient gas through electrolysis to maintain a desired membrane deflection behavior. The embodiments of the present disclosure provide a multilayer membrane actuator that can stop or slow the escape of hydrogen gas through the membrane, thereby reducing or preventing the eventual gas imbalance and reducing the need for constant power.

In particular, the regulating layer 544, which may be either impermeable or semipermeable to hydrogen gas, of the multilayer membrane actuator 510 prevents the inadvertent escape of hydrogen gas through the membrane. For example, in the embodiment pictured in FIG. 5, the regulating layer 544 comprises a thin film layer of gold sandwiched between first base and second base layers 540, 546, respectively, formed of Parylene, and the adherent layer 542 comprises a very thin deposit of titanium to provide adherence between the regulating layer 544 and the first base layer 540. Note that the composition and arrangement of the composite layers may be changed to achieve a desired level of gas permeation.

The gas permeability of the multilayer membrane may also be determined by the thickness of each individual layer and the thickness of the multilayer membrane 510. In FIG. 5, the composite layers 540, 542, 544, and 546 are depicted as being of substantially the same thickness for merely illustrative purposes. In various embodiments, the individual layers may have substantially similar thicknesses, or may have varying thicknesses. In particular, the thickness of the regulating layer 544 is ideally thin enough not to overly inhibit the expansion of the membrane, while being thick enough to inhibit the diffusion of gas through the membrane. For example, the thickness of the first base layer 540 may range from 1 to 10 µm, and may be approximately 3 µm. The thickness of the adherent layer 542 may range from 100 to 1000 Å, and may be approximately 500 Å. The thickness of the regulating layer 544 may range from 500 to 10,000 Å, and may be approximately 2,000 Å. The thickness of the second base layer 546 may range from 1 to 10 μm, and may be approximately 3 μm. In some embodiments, the thickness of the entire multilayer membrane ranges from 2 to 30 μm.

The gas permeability of the multilayer membrane may also be determined by the pattern of deposition or configuration of the individual layers, and in particular the regulating layer 544. For example, in some embodiments, the regulating layer 544 comprises a non-continuous layer instead of a continuous layer. For example, in some embodiments the regulating layer may be shaped as a grid-like layer or concentric rings In some embodiments, the multilayer membrane 510 (and the composite layers) includes corrugation features (such as ridges and valleys) whose depths affect the deflection profile of the membrane in response to various pressures.

In use, the IOP control system 200 is implanted in an eye in a conventional manner. The pressure sensors are disposed about the control system 200 in the manner described above. Particularly, the sensor P1 is disposed and configured to measure pressure in the interior eye, sensor P2 is disposed and configured to measure pressure within the valve system, sensor P3 is disposed and configured to measure atmospheric pressure, and sensor P4 is disposed and configured to measure bleb pressure.

The IOP control system is configured to adjust the flow through the valve system 230 based on measured pressure values or derivatives from the pressure sensors. If the pressures are not within desired ranges, the IOP control system 200 may adjust the valve system 230 to increase or decrease drainage flow through the drainage tube 330 to effect a pressure change to the desired pressure. To do this, the processor 215 operates the valve system 230 with the power source 205 to activate or deactivate the electrodes in the membrane valve 500 and/or the other structures 512. The electrodes act within the actuator fluid to change at least a portion of the fluid to a gaseous state, increasing the pressure within the flow control chamber. Over time these molecules recombine to change into a fluid state, decreasing the pressure and likewise the volume. To slow the state change, the diffusion barrier 536 may capture gaseous molecules within its passageways.

In operation, as the electrodes 534 generate bubbles in the actuator fluid 532 through electrolysis, the pressure increases within the chamber of the flow control chamber 530. As the liquid state partially changes to a gas state, the increasing pressure in the flow control chamber 530 acts against the flexible multilayer membrane 510 to displace it and increase the overall volume of the chamber. Thus, as the pressure increases, the multilayer membrane 510 expands into the fluid flow passageway 524, decreasing the cross-sectional area of the fluid flow passageway 524, and thereby restricting some fluid flow from the drainage tube 330. In a similar, but opposite manner, as the solution in the flow control chamber 530 returns to its more liquid state, the volume in the flow control chamber 530 decreases, permitting the multilayer membrane actuator 510 to move further out of the fluid flow passageway 524, thereby permitting an increased level of fluid flow from the drainage tube 330 through the passageway 524.

The regulating layer 544 of the membrane 510 slows or prevents the inadvertent loss of gas from the flow control chamber 530, thereby increasing the longevity and reliability of valve actuation by aiding the gas molecular ratio to stay in balance (e.g., one oxygen per two hydrogens). By aiding the gas molecular ratio to stay in balance within the flow control chamber 530, the regulating layer 544 reduces the overall amount of energy required to power the valve 500.

Moreover, in embodiments including the optional diffusion barrier 536, at least a portion of the gas interacts with the diffusion barrier 536 to prolong the state change back to liquid. This helps maintain pressure in the valve flow control systems for longer periods of time. Further, due to the state changes, the membrane 510 flexes or deflects to increase or decrease the cross-sectional area of the fluid flow passageway 524 to affect flow resistance, and ultimately control flow.

It is worth noting that for biocompatibility, the devices disclosed herein may be coated or encapsulated in a material such as polypropylene, silicon, parylene, or other materials.

The systems and methods described herein achieve IOP control with very low power and with a very small device. The electrolysis-based system accomplishes this using electrolysis and a multilayer membrane actuator to affect drainage flow. The system also may take into account bleb pressure and gas permeability in regulating drainage flow. The multilayer membrane allows for the reduction in gas permeability within the valve, thereby increasing the longevity and reliability of valve actuation by aiding the gas molecular ratio to stay in balance.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure

We claim:

1. An IOP control device for implantation in an eye of a patient, comprising:
   a housing sized for implantation into the eye of the patient and including an entrance port and an exit port; and
   a multilayer membrane anchored within the housing in a manner forming a flow control chamber on a first side of the multilayer membrane and a fluid flow passageway on a second opposing side of the membrane, the flow control chamber being arranged to contain an actuator fluid and a gas creating a flow control chamber pressure, the multilayer membrane configured to affect flow through the fluid flow passageway from the entrance port to the exit port by deflecting in response to changes in the flow control chamber pressure, the multilayer membrane comprising:
   a first base layer;
   an adherent layer;
   a regulating layer having a lower gas permeability and a lower flexibility than the first base layer, the regulating layer restricting diffusion of gas in the flow control chamber through the multilayer membrane; and
   a second base layer;
   wherein the adherent layer and the regulating layer are located between the first base layer and the second base layer, and the first base layer, the regulating layer, the adherent layer, and the second base layer form an integral membrane.

2. The IOP control device of claim 1, wherein the multilayer membrane is configured to reduce the gas permeability of the membrane to at least one type of gas.

3. The IOP control device of claim 2, wherein the regulating layer is shaped and configured to reduce the gas permeability of the membrane to hydrogen.

4. The IOP control device of claim 3, wherein the regulating layer includes gold.

5. The IOP control device of claim 2, wherein the regulating layer comprises a continuous layer in contact with the at least one of the first or second base layers.

6. The IOP control device of claim 2, wherein the at least one regulating layer comprises a non-continuous layer in contact with the first base layer.

7. The IOP control device of claim 1, wherein the adherent layer includes titanium.

8. The IOP control device of claim 1, wherein the multi-layer membrane is shaped and configured as a flexible, corrugated membrane.

9. The IOP control device of claim 1, wherein the flow control chamber includes an actuator fluid and an electrolysis system configured to affect the flow control chamber pressure by generating bubbles by converting at least a portion of the actuator fluid to the gas.

\* \* \* \* \*